United States Patent [19]

Redtenbacher et al.

[11] Patent Number: 4,817,847
[45] Date of Patent: Apr. 4, 1989

[54] INSTRUMENT AND A PROCEDURE FOR PERFORMING AN ANASTOMOSIS

[75] Inventors: Michael Redtenbacher, Vienna; Karl H. Munchow, Portschach, both of Austria

[73] Assignee: Finanzaktiengesellschaft Globe Control, Vaduz, Liechtenstein

[21] Appl. No.: 143,163

[22] PCT Filed: Apr. 21, 1987

[86] PCT No.: PCT/AT87/00029

§ 371 Date: Jan. 28, 1988

§ 102(e) Date: Jan. 28, 1988

[87] PCT Pub. No.: WO87/06448

PCT Pub. Date: Nov. 5, 1987

[30] Foreign Application Priority Data

Apr. 21, 1986 [AT] Austria ................... 1052/86
Mar. 19, 1987 [AT] Austria ................... 663/87

[51] Int. Cl.⁴ .............................. B31B 1/00
[52] U.S. Cl. ................. 227/19; 227/DIG. 1; 128/334 R
[58] Field of Search ............ 227/19, DIG. 1; 128/334 R, 335

[56] References Cited

U.S. PATENT DOCUMENTS

| | | | |
|---|---|---|---|
| 3,193,165 | 7/1965 | Akhalaya et al. | 227/8 |
| 4,574,806 | 3/1986 | McCarthy | 128/334 R |
| 4,606,343 | 8/1986 | Conta et al. | 227/DIG. 1 X |
| 4,667,673 | 5/1987 | Li | 128/334 C |

FOREIGN PATENT DOCUMENTS 7711347 10/1977 Netherlands .

Primary Examiner—Frank T. Yost
Assistant Examiner—James L. Wolfe
Attorney, Agent, or Firm—Laurence R. Brown; Alfred J. Mangels

[57] ABSTRACT

In order to perform an anastomosis, a pilot head of a surgical staple suturing instrument is connected through a push-type or a threaded connector and through a paraboloid-like cap so as to simplify introduction into the organ that is to be anastomised. The combination body is pushed through the organ with the help of a probe, as far as the end of the organ that has been sutured with a purse-string suture. Once the desired position of the pilot head is reached, the cap is released and then removed. The pilot head is then connected with the end of the journal of the staple suturing instrument through the push-type or threaded connector.

33 Claims, 5 Drawing Sheets

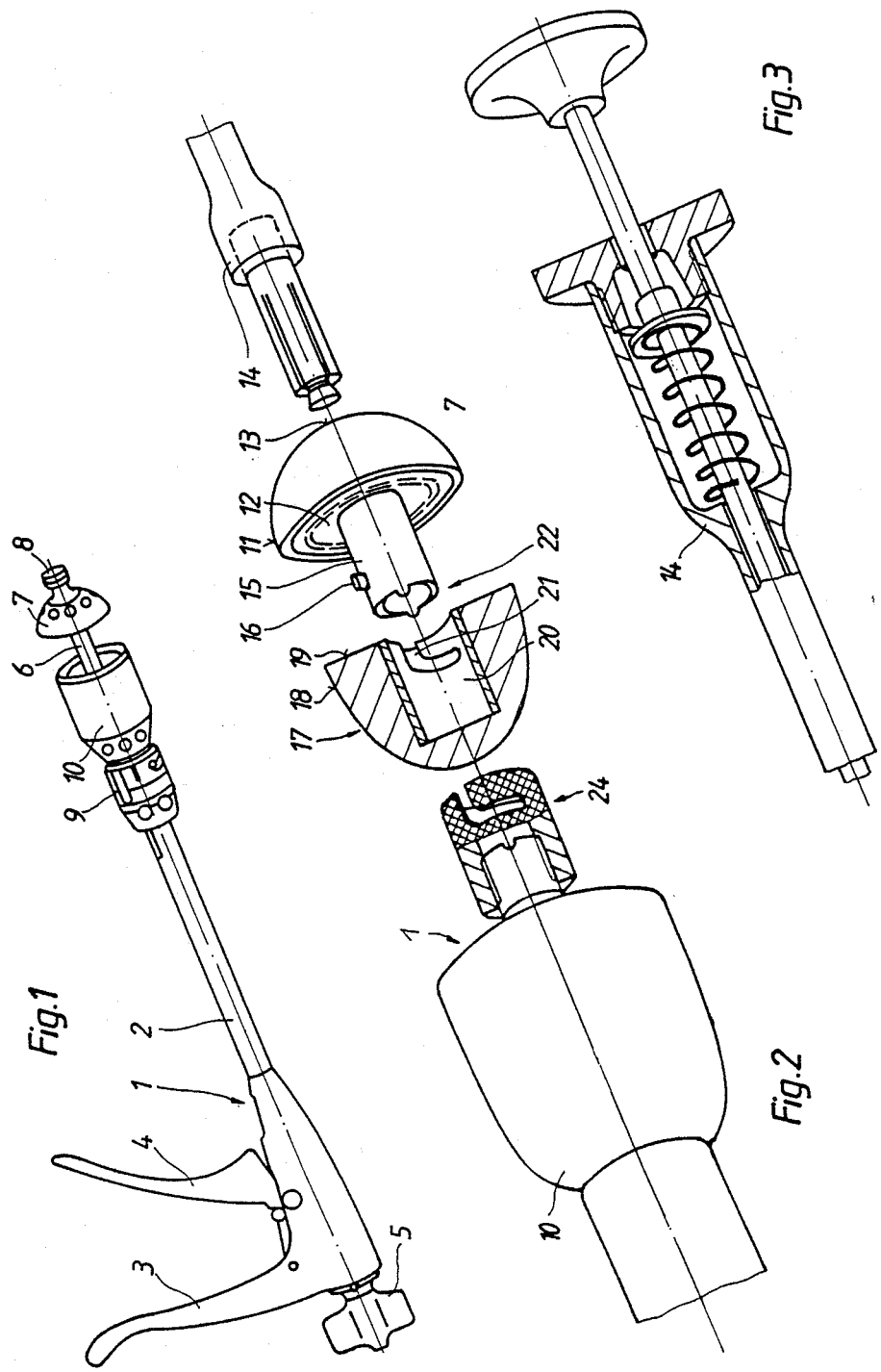

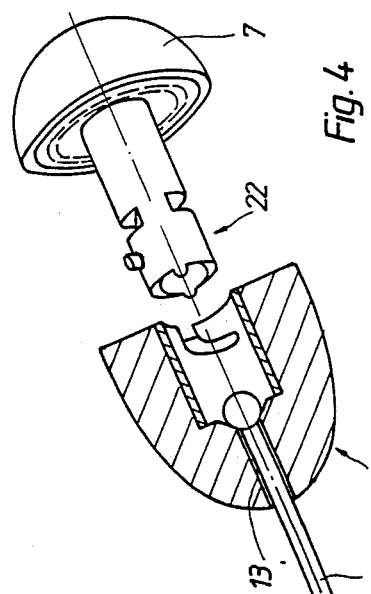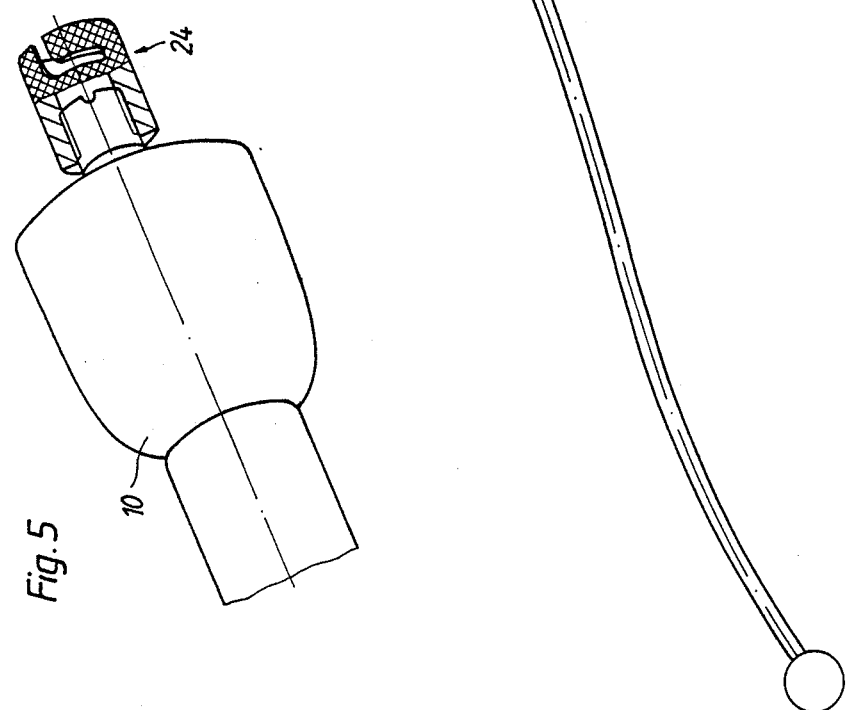

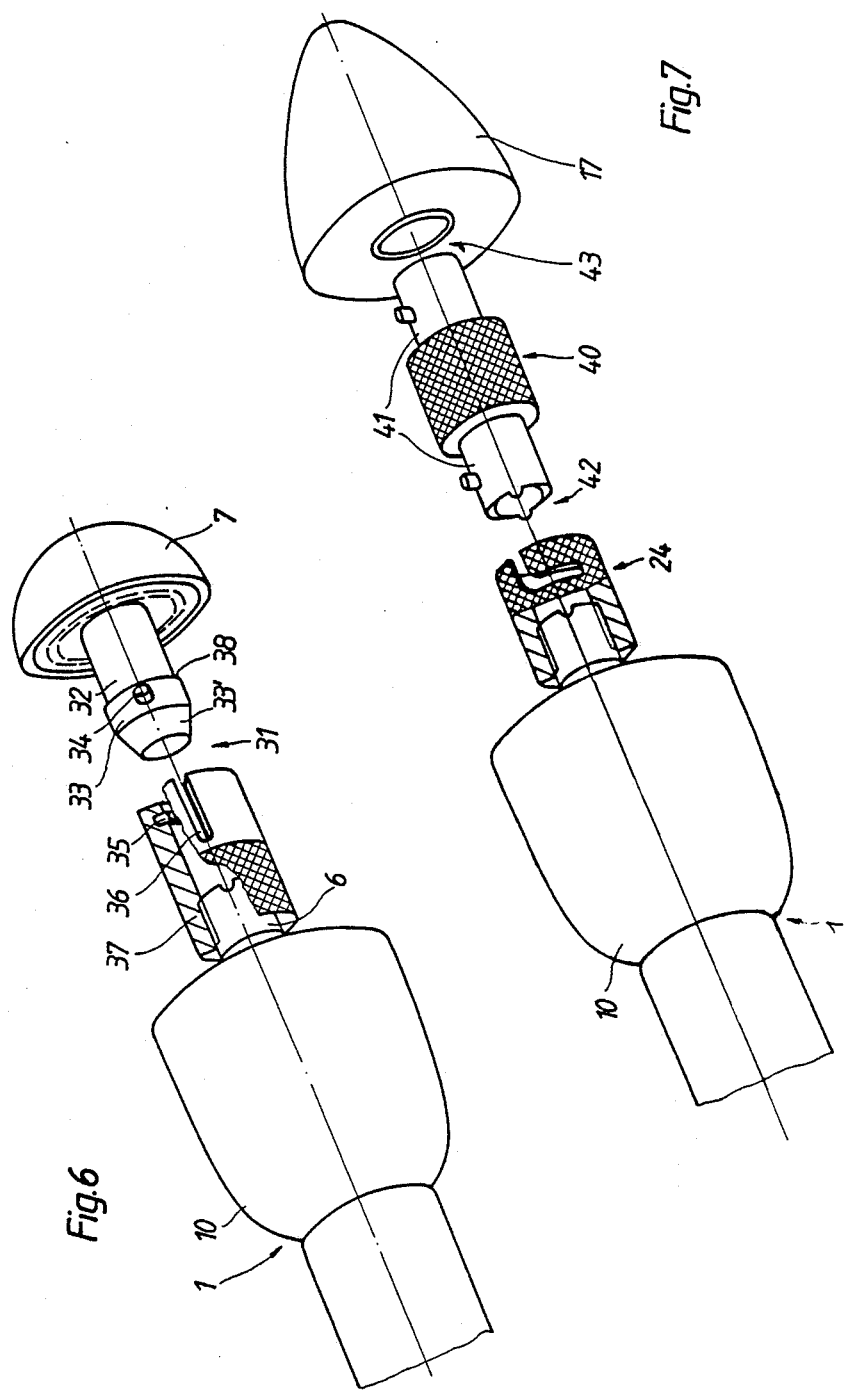

INSTRUMENT AND A PROCEDURE FOR PERFORMING AN ANASTOMOSIS

BACKGROUND OF THE INVENTION

1. Field of the Invention

The present invention relates to a surgical instrument for staple suturing, this having a central journal and a staple magazine that is secured to a handgrip, and a pilot head releasably secured at the end of the journal, this having a hemispherical outer surface and an anvil surface that is perpendicular to the axis of the journal and facing the staple magazine, said instrument being used to perform an anastomosis. The invention further relates to a stapling head for such an instrument.

2. Description of the Related Art

A staple suturing machine of this type is already known from U.S. Pat. No. 3,193,165. This instrument consists essentially of a cylindrical body having at one end a handle and a lever, in which a journal is received so as to be axially displaceable. At the end of the cylindrical body that is opposite the handle there is a staple magazine with a circular scalpel. The magazine contains stainless steel staples. A hemispherical pilot head is secured at the end of the journal. In order to perform an anastomosis, a purse-string suture is made at the the ends of, for example, the intestine ends that are to be joined. The staple suturing instrument is then introduced through an opening made in the side of one of the intestine ends, to the point that the tip of the pilot head emerges. Once the pilot head has been distanced slightly from the staple magazine, one end of the intestine is passed around the staple magazine and the other intestine end is passed around the pilot head and knotted about the journal by the purse-string suture. Next, the joining process is initiated, in that the pilot head is pressed against the staple magazine and the staples are forced into the structures that are to be anastomised. At the same time, the ends of the intestine with the sutures are separated by the circular scalpel. However, this known procedure entails the disadvantage that the whole of the pilot head has to be introduced through the purse-string suture of the second intestine end. The difficulty lies primarily in the difficulty of passing the second end of the intestine with the purse-string suture over the pilot head without damaging either the purse-string suture or the intestine.

It is the task of the present invention to produce a staple suturing instrument by which, while avoiding the disadvantages set out above, a relatively simple and problem-free introduction of the staple magazine and the pilot head into the required end of the organs to be anastomised is made possible.

SUMMARY OF THE INVENTION

According to the present invention, this task has been solved in that the pilot head can be connected through a push-type or threaded connector with the end of the journal, or with a cap that covers the staple cinching surface and surrounds the push-type connector with a curved outer surface. Because of the arrangement of the cap, the pilot head can be slid without any problem through the organ that is to be anastomised. Because of the push-type connector, once the pilot head has reached the required position at the end of the organ, the cap can be released both simply and rapidly, and the staple magazine and the pilot head can be connected just as easily and rapidly.

According to a further advantageous variation of the invention, it is foreseen that thepush-type connector is configured as a bayonet fastening. A connector of this type is particularly well suited as a push-type connector, since only a very slight rotation of the parts to be connected is needed in order to produce a firm and reliable connection.

According to a further advantageous embodiment of the present invention it is foreseen that the push-type connector is configured as a journal that is connected with the pilot head and has a mushroom end and a locating pin that extends perpendicularly to the longitudinal axis of the journal, and as a socket that can be connected with the end of the journal and which has a circlip and a slot. A push-type connector of this kind is particularly advantageous in that all that it needs is that the socket and the journal be pushed into each other slightly, without any rotation. When this is done, the locating pin ensures that the pilot head is correctly oriented with reference to the staple magazine.

According to another advantageous embodiment of the invention the push-type connector can be configured as a journal-like first part that can be releasably connected to the pilot head by a threaded section, and a second part of the push-type connector that can be releasably connected to the end of the journal through a threaded section. This push-type connector is suited in a particularly advantageous manner for retrofitting to known staple suturing instruments that are already in use. Such retrofitting entails very little cost and can be completed very simply.

According to an advantageous variation of the invention the cap can be configured as a paraboloid-like rotational body which, when in the operating position, has a base surface that is adjacent to the staple cinching surface or plane of the pilot head and which is parallel to this, the base surface having a drilled hole that is perpendicular to this and central to the cap, with one part of a push-type connector, e.g., a guide for the journal of a bayonet fastener. A cover that is configured in this manner, which is similar to a paraboloid, is particularly suitable for the careful insertion of the pilot head into the organ that is to be anastomised, the journal that extends from the pilot head, which is required for subsequent connection with the staple magazine, being accommodated by the drilled hole that extends centrally.

According to a further preferred embodiment of the invention, a cylindrical adapter having at each end a journal of a bayonet fastener can be provided as an adapter to connect the staple magazine and the cover. Using such an adapter, the staple magazine can be connected to the cover in a particularly advantageous manner so as to ensure the simpler and more careful insertion of said staple magazine into the organ that is to be anastomised.

Furthermore, in accordance with the present invention, it is also advantageous if the connecting elements of the push-type connecter, which are releasably fixable on the ends of the journal or the cover, have a knurled surface. Such a roughened surface of the connecting elements ensure their reliable connection with the ends of the journal or the cover, without the need to use any tools therefore.

A further advantageous embodiment of the present invention comprises the features set out in claim 8. The separate introduction and the separate withdrawal of the staple magazine, on the one hand, and of the pilot head, on the other, now made possible by the present invention, means that the anastomosis is far simpler to perform, while avoiding excessive strain on the purse-string suture that has been put in position. Since the pilot head has already been introduced into the organ already foreseen for this head, there is no need to fold the organ over the pilot head, which was formerly required and was relatively inconvenient, in order to permit tying the suture. Of particular advantage, however, is the fact that because of the instrument according to the present invention, once the anastomosis has been performed the pilot head can be moved away from this, thus safeguarding the site of the joint that has just been completed, to the other outlet of the organ in question. Simultaneously, the connection of the guide journal with an endoscope entails the especial advantage the the site of the anastomosis (e.g., the oesophagus) can be inspected from the inside prior to performance of the anastomosis. In addition, the recently completed anastomosis can be inspected visually, once the instrument that bears the staple magazine has been removed, in order to detect any possible complications and eliminate these, or in order to obtain a photographic record of the procedure.

Rapid connection of both parts is possible with a further configuration of the end of the guide journal or the end area of the endoscope, as is shown in FIG. 9, this being possible without detriment to the function of the endoscope. In the same manner, once the anastomosis has been completed, it is possible to uncouple the parts very rapidly with the help of a withdrawal system, so that the guide journal together with the instrument and the staple magazine is removable by way of the opposite organ.

A pilot head configured as herein described can be installed on endoscopes that are already in use, without any particular construction costs and without detriment to the function of said endoscopes.

The measures set out hereinafter permit constant visual monitoring of the staple suturing instrument, both during insertion and when making the sutures, and render it simple to do so.

This permits the anastomosis of organs as is hereinafter described.

BRIEF DESCRIPTION OF THE DRAWINGS

The present invention will be described in greater detail in conjuction with embodiments shown in the accompanying drawings, wherein:

FIG. 1 is a side view of a known surgical staple suturing instrument;

FIGS. 2 and 3 are perspective views of a staple magazine, a pilot head, and a cap;

FIGS. 4 and 5 are also perspective views of a pilot head and a cap according to another embodiment;

FIG. 6 is a perspective view of another embodiment showing the pilot head and the connector;

FIG. 7 is a perspective view of a pilot head and a cap (stapling head) according to still another embodiment;

DESCRIPTION OF THE PREFERRED EMBODIMENTS

Figure 8:
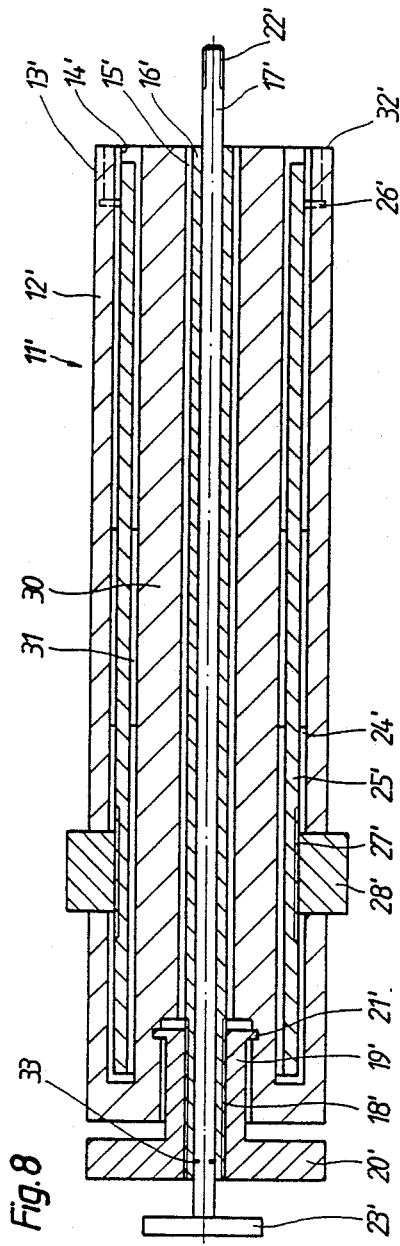
FIG. 8 is a longitudinal cross-section through a staple suturing instrument of this invention.

A surgical suturing instrument 1 of the known kind, which can be seen in FIG. 1, consists essentially of a cylindrical body 2 and a handle 3 that is arranged at one end of this, a movable lever 4, and a wing nut 5. A coaxially guided spindle 6 is received in the cylindrical body 2 so as to be longitudinally slidable, and a hemispherical pilot head 7 is releasably secured to this by means of a threaded nut 8. At the end of the cylindrical body 2 that is opposite the handle 3 there is a turn-lock fastener 9, this being releasably connected to a staple magazine 10. In order to complete an anastomosis, the organs that are to be connected must be guided, on the one hand, over the staple magazine 10, on the other hand, over the pilot head 7 and tied by a purse-string suture in the area of the journal that is located between these two. Next, the pilot head 7 is moved towards the staple magazine 10 by rotation of the wing nut 5. When the movable lever 4 is operated, the staples located within the staple magazine 10 are introduced into the ends of the organs that are to be sutured together, these organs being joined together thereby. At the same time, the internal structures of said organs with the purse-string sutures are removed by a circular scalpel.

The cap 17 that is shown in FIG. 2, which has a hemispherical surface 11 and an anvil surface 12 for cinching the staples, is connected through the drilled hole 13 to a probe 14 and, in the area of of the anvil surface 12, with a journal 15. At its unattached end, this has a locating pin 16 that protrudes perpendicularly to the direction of the axis. A cap 17 having a curved outer surface 18 and a base surface 19 has a central drilled hole 20 with a bayonet-fastener guide slot 21 for the locating pin 16. The slot 21 and the journal 15 together form a push-type connector 22 that is configured as a bayonet fastener.

The journal 6 that protrudes from the staple magazine 10 is connected by a thread 23 to a cylindrical section 25 that is configured as a part 24 of a push-type connector; this section 25 is provided so as to accommodate the journal 15 and has a guide slot 26 that accommodates the locating pin 16. Thus, the journal 15 of the pilot head 7 also forms a push-type connector 22 with the end of the journal 6 and the part 24 of the push-type connector. In order to utilize the instrument of this invention, the pilot head 7, already connected with the probe 14, is connected through the push connector 22 to the cap 17, whereupon the base surface 19 of the cap 17 abuts on the anvil surface 12. With the help of the probe (the end of the probe 14 that facilitates this introduction is shown in FIG. 3), the resulting egg-shaped body comprising the pilot head 7 and the cap 17 is introduced into the organ that is to be anastomised, in the direction of an end where an appropriate purse-string suture has already been put in place. As soon as the correct position for the pilot head 7 has been reached, the cap 17, which is now protruding from the end of the organ, is rotated about the longitudinal axis of the push connector 22, released, and removed. In the meantime, the suturing instrument has been introduced into the other organ, to the point that the staple magazine 10 is correctly positioned. After the cap 17 has been removed, a connection between the end of the journal and the pilot head 7 is made by introducing the journal 15 into the cylindrical section 25 and rotating the instrument 1. The organs are next tied around the journal 6, this being done in the already known manner described heretofore. Once this joint has been made, the pilot head 7 can be removed from the organ in the reverse direction, by releasing the probe 14 with the staple suturing instrument, or by releasing the push connector 22, once again by the probe.

The pilot head 7 that is shown in FIG. 4 is also connectable to the cap 17 through a push-type connector that is configured as a bayonet fastener. However, these, together with the pilot head 7 are drawn in the direction of the ends of the organs that are to be anastomised by means of a traction element 30 that is introduced through a drilled hole 13. Once the pilot head 7 has reached the desired position, this is once again connected with the staple magazine 10 through the push-type connector shown in FIG. 5.

A push connector 31 that is shown in FIG. 6 is configured as a journal 32 that is connected to the pilot head 7 with a mushroom end 33 and a locating pin 34 that extends perpendicularly to the longitudinal direction of the journal, and as a socket 37 that is connected to the end of the journal 6, said connector incorporating a slot 36 and a circlip 35.

The mushroom end 33 has a truncated conical extension 33' and a step 38. Once the two parts have been connected, the circlip 35 snaps into position behind the step 38.

FIG. 7 shows a cylindrical distance piece 40 that has a journal 41 at each end. Each such journal 41 is an element of a bayonet fastening 42, 43, connectable on one side with the cover 17 and on the other with the end of the journal 6. In this way, both the end of the journal and the staple magaazine 10 can be covered so as to provide for safer introduction of the instrument into the organ that is to be sutured.

The part of the suturing machine or the stapling instrument 11', respectively, according to the present invention and shown in FIG. 8, consists of a cylindrical housing 12' that is connected at one end with a staple magazine 13' and a circular scalpel 14'. Centrally within this cylindrical housing 12' there is a drilled hole 15'. A hollow journal 16' that is secured so as to be unable to rotate is received in this drilled hole 15' so as to be longitudinally slidable; a journal 17' is accommodated within the internal diameter of said hollow journal 16'. At one end, this hollow journal 16' has a threaded section 18'. This engages in the threaded section of a cylinder 19', which at its end is connected to the wing nut 20'. The hollow journal 16' can be displaced longitudinally by turning this wing nut 20', which is rotatably received in the housing 12' at 21'. The journal 17' that is received in the hollow journal 16' has a knurled knob 23' at the end at which the wing nut 20' is attached to the hollow journal, and at the other end has a threaded section 22'. However, in place of this, a push- or bayonet fastener can be used. The journal 17' described immediately heretofore serves to connect a guide journal and an anvil, which will be described below in connection with FIG. 3.

Between the central drilled hole 15' and the outer surface of the cylindrical covering of the housing 12' there is a cylindrical opening 24', within which is supported a guide cylinder 25'. This is connected through a schematically represented operating system 26' with the staple magazine 13' and the scalpel 14'. On the outside of the casing of the guide cylinder 25' there is a threaded section 27' that is connected with an annular body 28' that has its outside surface arranged outside the housing 12'. The guide cylinder 25' has slots that extend in an axial direction, and the cross pieces 31', which join the outer wall of the housing with the inside body of the housing 30', pass through these. These cross pieces 31' simultaneously serve to prevent rotation of the guide cylinder 25'. The guide cylinder 25' is displaced by rotating the annular body 28'. When this is done, the metal staples 32' are advanced from the staple magazine 13' through the slots that are provided, and the circular scalpel 14' is moved forward to make the separating incision. Viewed in a longitudinal direction, the journal 17' is connected with the cylinder 19' through a ring 33' that is connected with the cylinder 19', said ring 33' engaging in a corresponding annular groove in the journal 17 although it can rotate freely relative to this through the knurled knob 23'.

Figure 9:
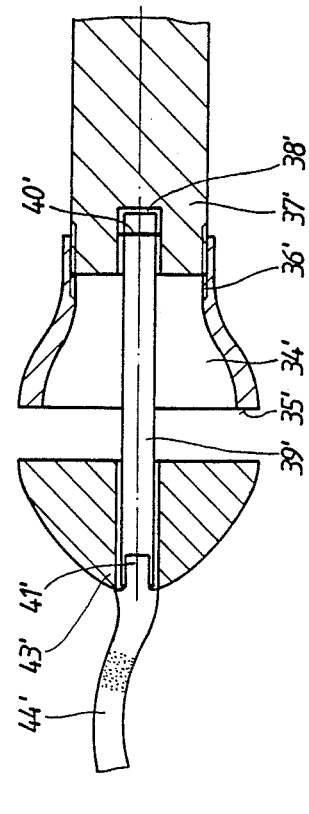
FIG. 9 is a cross-section through a pilot head connected to an endoscope.

FIG. 9 shows the actual pilot head 34' that forms part of the stapling instrument or suturing instrument 1'. This is hemispherical and has in the end area that is opposite the anvil surface 35' that cinches the staples an opening with a thread 36' for releasable fixing at the end of an endoscope 37'. However, the threaded connection that is shown can also be configured as a bayonet fastening or the like. At its end, the guide journal 39' has a bayonet fastening 40' that can be inserted into a central drilled hole 38' in the endoscope 37'. At its end that is opposite the fastening 40' the guide journal 39' has a threaded section. However, a threaded pin can also be screwed into this blind hole 41'. This has a stylet 44 that connects centrally on the convex outer surface of the insertion body 43' and a threaded pin 42' that is opposite the attachment point for the stylet 44' and is used to secure the insertion body 43' to the guide journal 39'.

Figure 10:
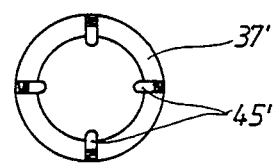
FIGS. 10 and 11 show an enlarged detailed view of the guide journal.
Figure 11:
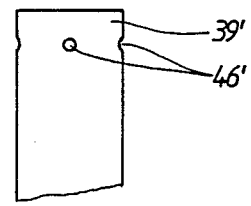

As can be seen in a further embodiment as in FIGS. 10 and 11, within the end area of an endoscope 37' there are four pegs 45 arranged such that they are spring-loaded and extend into the clear area of a central drilled hole in the endoscope 37'. These pegs 45' enter into a detent in corresponding drilled holes 46' at one end of the guide journal 39'. This makes it possible to connect the endoscope to the guide journal very rapidly. If the guide journal 39' is to be released, the pegs 45' are withdrawn from the central drilled hole in the endoscope 37' with the help of a withdrawal system.

Figure 12:
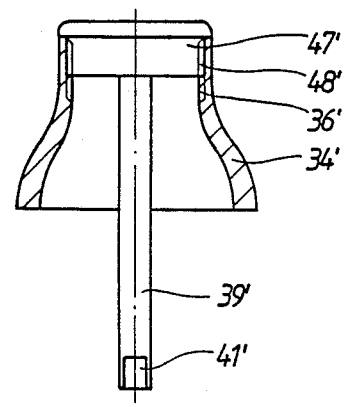
FIG. 12 shows a modified embodiment of a guide journal in combination with a pilot head.

FIG. 12 shows a somewhat modified guide journal 39', this being used if the stapling instrument or system 11' is to be used without the endoscope 37'. The guide journal 39' has a stopper 47' with a threaded section 48' in the end area that is opposite the blind hole 41'. This stopper 47' can be screwed into an opening with a threaded section 36' in the pilot head 34'.

The method of utilizing the instrument 1' configured according to the present invention will be described below on the basis of a circularly sutured anastomosis with the oesophagus. A purse-string suture is first emplaced in the oesophagus and in the second section of the intestine. The guide journal 39' is then installed in the drilled hole 38' of the endoscope 37'. The pilot head 43' is next screwed onto the endoscope 37'. These preparations are carried out on a sterile table by an endoscopologist. The insertion body 43' is then fixed in position by inserting the threaded pin 42' into the blind hole 41' in the guide journal 39'. The suturing instrument 11' with the staple magazine 13' is introduced into the second section of the intestine, when a purse-string suture is knotted about the journal 17'. The prepared endoscope 37' with the pilot head 34' is inserted through the mouth with the help of the stylet 44'. When this is done, the stylet 44' is advanced to the point that the operator can grasp it at the end of the oesophagus, on which the purse-string suture is located. The pilot head 34' and the endoscope 37' are moved forward by the stylet 44' until the insertion body 43' is pushed out of the end of the oesophagus. The next step is to tie the purse-string suture on the end of the oesophagus, between the insertion body 43' and the pilot head 34'. As soon as the two purse-string sutures are ready, the insertion body 43' is released from the guide journal and removed. Next, the journal 17' of the instrument 11' is screwed [on] with the guide journal 39'. This is done by rotating the journal with the help of the knurled knob 23'. Endoscopic examination of the wall of the oesophagus can be carried out with the help of the endoscope 37'. The anastomosis is completed by rotating the annular body 28'; when this is done, the forward movement of the guide cylinder 25' forces the staples from the corresponding slots and the internal structure of the organs is separated by the circular scalpel 14'. the endoscope 37' is uncoupled by rotation of the two screwed-together journals 17' and 39' with the help of the knurled knob 23', and the suturing insturment together with the guide journal 39' are removed from the intestine. To this end, the bayonet fastening 40' and the thread 22' close in opposing directions. the endoscope 37' and the pilot head 34' that is docked on this remain above the anastomosis. An inspection of the anastomosis can be carried out with the endoscope. Any complications can be detected with the endoscope 37'. It is also possible to make a photographic record of the site.

A further example is the completion of a circularly sutured anastomosis with the rectum. First, a purse-string suture is emplaced in the rectum and in the section of the gut that is to be joined to the rectum. Next, the guide journal 39' is docked on the pilot head 34' (FIG. 12). The section of the gut that is to be anastomised is secured with the opening towards the surgeon, and the pilot head 34' is inserted with great care into this opening. The purse-string suture is then tied. The portion of the suturing instrument 11 that bears the staple magazine 13 is connected to the journal 39' with the inflatable insertion body 43' and introduced through the anus. The knotting of the purse-string suture is followed by removal of the insertion body 43'. Next, the anastomosis is completed in the manner described above. In this connection, it is a particular advantage that the pilot head 34' is introduced into the gut when in view and the purse-string suture can be tied when in view. Once the gut has been closed by the purse-string suture, this can be led without any problem into the small pelvis without any fecal matter escaping from the gut.

The embodiments of the invention in which an exclusive property or privilege is claimed are defined as follows:

1. A staple suturing instrument for performing an anastomosis, said instrument comprising: a staple magazine including a central journal and a circular scalpel, a pilot head releasably secured at an end of the central journal, said pilot head having an hemispherical outer surface and an anvil surface for clinching staples, said anvil surface facing the staple magazine, wherein the pilot head is releasably attached through a connector with the end of the central journal and with a cap that covers the anvil surface and the connector wherein said cap has a curved outer surface.

2. A staple suturing insturment as defined in claim 1, wherein the connector a bayonet fastening.

3. A staple suturing instrument as defined in claim 1, wherein the connector includes a second journal having a mushroom end and a locating pin that projects perpendicularly to the longitudinal axis of the second journal and is connected to the pilot head, and includes a socket on the end of the central journal, the socket having a circlip and a slot.

4. A staple suturing instrument as defined in claim 1, wherein the connector includes a first connector element that is releasably connected with the pilot head and a second connector element releasably connected with the guide journal end.

5. A staple suturing instrument as defined in claim 4, wherein the first and second connector elements that are releasably fixable on the end of the guide journal and the cap have a knurled external surface.

6. A staple suturing instrument as defined in claim 1, wherein the cap is configured as a paraboloid-like rotational body with, in the operating position, a base surface that is adjcent to the anvil surface of the pilot head and parallel thereto, the base surface including an opening that is perpendicular to the base surface and extending centrally to the cap and having a guide means for a bayonet fastening.

7. A staple suturing instrument as defined in claim 1, including a cylindrical adapter with a bayonet fastening means at each end and provided as a connector to join the staple magazine and the cap.

8. A staple suturing instrument as defined in claim 1, including a guide journal axially connectable onto the end of the central journal that protrudes out of the staple magazine, the other end of said journal being couplable with an endoscope that is connected to the pilot head.

9. A staple suturing instrument as defined in claim 8, wherein the guide journal has drilled holes in its end area that is adjacent to an operating channel of the endoscope, and springloaded pins that are arranged in an end area of the endoscope, the pins entering into detent means in said drilled holes and being removable from the drilled holes by a return means.

10. A staple suturing instrument as defined in claim 8, wherein the pilot head has in its end area that is opposite the anvil surface for the staples an opening that accommodates one of a threaded section, a bayonet fastening and a quick-acting connector fastener, for releasable installation at the end of the endoscope.

11. A staple suturing instrument as defined in claim 8, including a hemispherical insertion body having a convex outer surface and a stylet that is connected centrally to the convex outer surface and opposite an attachment point for the stylet, and a threaded pin for attaching the insertion body on the guide journal.

12. A staple suturing instrument as defined in claim 8, wherein the central journal is supported within a hollow journal at an end adjacent the staple magazine and includes a disc that is perpendicular to the longitudinal axis at the other end; and the end of the hollow journal adjacent the disc is connected through a threaded section to a wing nut that is supported on the housing.

13. A staple suturing instrument as defined in claim 8, including a housing having a cylindrical opening containing a guide cylinder having a circular scalpel connected at one end and at the other end having on its outer surface a threaded portion that engages with an annular body having its outer surface arranged outside the housing, and the guide cylinder is engageable with the staple magazine.

14. A staple suturing instrument as defined in claim 1, including and endoscope, and wherein the staple suturing instrument is connected to the endoscope.

15. A method for performing an anastomosis by the introduction of a surgical staple suturing instrument having a central journal into an organ that is to be anastomised, said method of comprising: (a) providing a purse-string suture at the organ end to be joined, (b) folding the end of the organ about a staple magazine, (c) providing a purse-string suture at the free end of the other organ that is to be anastomised, (d) folding the other organ end about a hemispherical pilot heat that has a staple cinching surface that is connected to the staple magazine through a journal, (e) connecting the pilot head with a cap having a convex surface that covers the staple cinching surface, (f) introducing the pilot head and cap into the second organ in the direction of the free end that has the purse-string suture, and independently of the staple magazine that is connected with the staple suturing instrument that is introduced a desired distance into the first organ that is to be anastomised, (g) removing the cap from the pilot head, (h) connecting the pilot head to the central journal of the staple suturing instrument, and (i) effecting a stapled joint of both organ ends by pressing the pilot head onto the staple magazine.

16. A procedure as defined in claim 15, including the step of connecting the cap to a probe and introducing the cap and probe into the organ that is to be anastomised.

17. A procedure as defined in claim 15, wherein after a purse-string suture has been prepared on both the organs that are to be anastomised, inserting the instrument for performing the anastomosis into one organ; advancing the instrument as far as the purse-string suture; and introducing the pilot head into the other organ with the help of an endoscope; advancing the pilot head as far as the corresponding purse-string suture; connecting the pilot head to the journal of the instrument; performing the anastomosis; and releasing the pilot head from the guide journal; and withdrawing the pilot head independently of the instrument and with the help of the endoscope.

18. A procedure as defined in claim 17, including the step of securing an insertion body, which is configured as a mirror image of the pilot head, to the guide journal that is connected to the pilot head and the endoscope on introduction into the organ, and removing the insertion body from the guide journal once the required position for the pilot head has been reached.

19. A precedure as defined in claim 15, including the step 2 introducing the endoscrope into the organ to be anastomised with at least part of the staple suturing instrument.

20. A stapling head for a staple suturing instrument for performing an anastomois, said instrument comprising: a staple magazine including a central journal and a circular scalpel, a pilot head releasably secured at an end of the central journal, said pilot head having an hemispherical outer surface and an anvil surface for clinching staples, said anvil surface facing the staple magazine, wherein the stapling head is constructed in two parts, and wherein the pilot head is connectable with the end of the central journal and with a cap having a curved outer surface that covers the anvil surface.

21. A staple suturing instrument as defined in claim 20, wherein the connector is a bayonet fastening.

22. A staple suturing instrument as defined in claim 20, wherein the connector includes a second journal having a mushroom end and a locating pin that projects perpendicularly to the longitudinal axis of the second journal and is connected to the pilot head, and includes a socket on the end of the central journal, the socket having a circlip and a slot.

23. A staple suturing instrument as defined in claim 20, wherein the connector includes a first connector element that is releasably connected with the pilot head, and a second, connector element releasably connected with the guide journal end.

24. A staple suturing instrument as defined in claim 23, wherein the first and second connector elements that are releasably fixable on the end of the guide journal and the cap have a knurled external surface.

25. A staple suturing instrument as defined in claim 20, wherein the cap is configured as a paraboloid-like rotational body with, in the operating position, a base surface that is adjacent to the anvil surface of the pilot head and parallel thereto, the base surface including an opening that is perpendicular to the base surface and extending centrally to the cap and having a guide means for a bayonet fastening.

26. A staple suturing instrument as defined in claim 20, including a cylindrical adapter with a bayonet fastening means at each end and provided as a connector to join the staple magazine and the cap.

27. A staple suturing instrument as defined in claim 20, including a guide journal axially connectable onto the end of the central journal that protrudes out of the staple magazine, the other end of said journal being couplable with an endoscope that is connected to the pilot head.

28. A staple suturing instrument as defined in claim 27, wherein the guide journal has drilled holes in its end area that is adjacent to an operating channel of the endoscope, and springloaded pins that are arranged in the end area of the endoscope, the pins entering into detent means in said drilled holes, and being removable from the drilled holes by a return means.

29. A staple suturing instrument as defined in claim 27, wherein the pilot head has in its end area that is opposite the anvil surface for the staples an opening that accommodates one of a threaded section, a bayonet fastening and a quick-acting connector fastener, for releasable installation at the end of the endoscope.

30. A staple suturing instrument as defined in claim 27, including a hemispherical insertion body having a convex outer surface and a stylet that is connected centrally to the convex outer surface and opposite an attachment point for the stylet, and a threaded pin for attaching the insertion body on the guide journal.

31. A staple suturing instrument as defined in claim 27, wherein the central journal is supported within a hollow journal at an end adjacent the staple magazine and includes a disc that is perpendicular to the longitudinal axis at the other end; and the end of the hollow journal adjacent the disc is connected through a threaded section to a wing nut that is supported on the housing.

32. A staple suturing instrument as defined in claim 27, including a housing having a cylindrical opening containing a guide cylinder having a circular scalpel connected at one end and at the other end having on its outer surface a threaded portion that engages with an annular body having its outer surface arranged outside the housing, and the guide cylinder is engageable with the staple magazine.

33. A staple suturing instrument as defined in claim 20, including an endoscope, and wherein the staple suturing instrument is connected to the endoscope.

* * * * *